US 7,854,715 B2

(12) United States Patent
Ashihara (10) Patent No.: US 7,854,715 B2
(45) Date of Patent: Dec. 21, 2010

(54) WALK SUPPORTING DEVICE

(75) Inventor: Jun Ashihara, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 186 days.

(21) Appl. No.: 11/841,288

(22) Filed: Aug. 20, 2007

(65) Prior Publication Data
US 2008/0051686 A1 Feb. 28, 2008

(30) Foreign Application Priority Data

Aug. 22, 2006 (JP) ............................. 2006-224801
May 22, 2007 (JP) ............................. 2007-135579

(51) Int. Cl.
*A61F 5/00* (2006.01)
*A61H 1/00* (2006.01)
*A45B 1/00* (2006.01)
*A63B 22/00* (2006.01)

(52) U.S. Cl. .................. 602/23; 601/5; 601/33; 601/34; 601/35; 135/65; 482/51

(58) Field of Classification Search ............... 602/28, 602/23; 135/65; 482/66; 601/5, 31, 33–35
See application file for complete search history.

(56) References Cited

U.S. PATENT DOCUMENTS

| | | | | | |
|---|---|---|---|---|---|
| 4,872,665 | A | * | 10/1989 | Chareire | 482/51 |
| 4,875,665 | A | * | 10/1989 | Kato et al. | 267/170 |
| 6,117,052 | A | * | 9/2000 | Frost et al. | 482/52 |
| 6,220,990 | B1 | * | 4/2001 | Crivello | 482/51 |
| 6,666,796 | B1 | * | 12/2003 | MacCready, Jr. | 482/51 |
| 6,679,813 | B1 | * | 1/2004 | Gray | 482/71 |
| 6,770,040 | B2 | * | 8/2004 | Perner et al. | 601/5 |
| 7,425,189 | B1 | * | 9/2008 | Eschenbach | 482/52 |
| 2005/0014613 | A1 | * | 1/2005 | Chu | 482/79 |
| 2006/0064047 | A1 | * | 3/2006 | Shimada et al. | 602/23 |
| 2008/0020902 | A1 | * | 1/2008 | Arnold | 482/51 |

FOREIGN PATENT DOCUMENTS

JP 5-329186 12/1993
JP 2003-220102 8/2003

* cited by examiner

*Primary Examiner*—Patricia M Bianco
*Assistant Examiner*—Victoria Hicks
(74) *Attorney, Agent, or Firm*—Rankin, Hill & Clark LLP (57) ABSTRACT

A walk supporting device includes a seating member on which a user is seated in a straddling manner and a pair of left and right leg links that support the seating member from below. Each of the leg links is coupled to the seating member to freely swing in a horizontal direction. The seating member is prevented from rolling around a support shaft serving as a swing fulcrum in the horizontal direction of the leg link to improve stability in the horizontal direction of the seating member. A stopper member coupled to the seating member is inserted between joint sections at upper ends of left and right leg links supported by the support shaft. A regulating mechanism that regulates the seating member in a posture orthogonal to an equiangular bisector of an angle in the horizontal direction formed by the left and right leg links may be provided.

9 Claims, 6 Drawing Sheets

WALK SUPPORTING DEVICE

BACKGROUND OF THE INVENTION

1. Field of the Invention

The present invention relates to a walk supporting device that supports walk of a user.

2. Description of the Related Art

Conventionally as a walk supporting device of this type, there is known a walk supporting device that includes a waist support belt worn around the waist of the user and a pair of left and right leg links coupled to the waist support belt on both sides in a horizontal direction via joint sections equivalent to human hip joints (see, for example, Japanese Patent Laid-Open No. 2003-220102).

In the walk supporting device of the conventional example described above, it is necessary to wear the waist support belt around the waist tight in order to surely transmit supporting forces generated by the leg links to the body of the user. Thus, the user tends to feel restraint. Moreover, since the joint sections at the upper ends of the left and right leg links protrude on both sides of the waist of the user, the hands of the user tend to hit the joint sections and upper portions of the leg links coupled to the joint sections when the user swings the arms during walk. This leads to poor usability.

Conventionally, there is also known a walk supporting device that includes four support legs having wheels at lower ends thereof and vertically provided on a frame surrounding a user from a rear side to both ends in a horizontal direction and a saddle-like seating member attached to the frame on which the user is seated in a straddling manner, detects a force applied to the seating member by the user, and drives the wheels to increase the force to a predetermined target value (see, for example, Japanese Patent No. 3156367).

In this walk supporting device, although it is possible to reduce the restraint felt by the user, it is impossible to use the walking support device in a narrow space because of a large size thereof. Further, since the hands of the user tend to hit the frame when the user swings the arms during walk, usability is not satisfactory.

As described above, the conventional walk supporting devices have various deficiencies. Therefore, the inventors have reached an idea of a walk supporting device that supports a seating member, on which the user is seated in a straddling manner, from below with a pair of left and right leg links. According to this walk supporting device, it is possible to surely transmit supporting forces generated by the leg links from the inner side of leg to the body of the user via the seating member. The user only has to be seated on the seating member in a straddling manner. Thus, the restraint felt by the user is reduced. The leg links coupled to the seating member are located in the inside leg of the user. Thus, the hands do not hit upper portions of the leg links when the user swings the arms during walk and can freely swing the arms. In addition, the walk supporting device is small in size unlike the conventional walk supporting devices including the frames surrounding a user and can be used even in a narrow place. Therefore, convenience of use is remarkably improved in conjunction with the reduction in the restraint and the ensuring of the freedom of swing of arms.

It is desirable that the leg links are coupled to the seating member to freely swing in the horizontal direction. This makes it possible to turn the legs of the user outward and increases a degree of freedom in movement of the legs of the user. However, this causes the following deficiencies.

The seating member is capable of rolling in the horizontal direction around a swing fulcrum in the horizontal direction of the leg links. Thus, when a point of action of a body weight on the seating member shifts in the horizontal direction with respect to the swing fulcrum in the horizontal direction of the leg links, the seating member greatly tilts in the horizontal direction.

SUMMARY OF THE INVENTION

The present invention has been devised in view of the problems and it is an object of the present invention to provide a small and convenient walk supporting device that can improve, although leg links are coupled to a seating member to freely swing in the horizontal (lateral)direction, stability in the horizontal direction of the seating member.

The present invention provides a walk supporting device including a seating member on which a user is seated in a straddling manner and a pair of left and right leg links that support the seating member from below, each of the leg links being coupled to the seating member to freely swing in a horizontal direction, characterized as described below in order to achieve the object. According to a first aspect of the present invention, a stopper member coupled to the seating member is inserted between the left and right leg links. According to a second aspect of the present invention, the walk supporting device includes a regulating mechanism that regulates the seating member in a posture orthogonal to an equiangular bisector of an angle in the horizontal direction formed by the left and right leg links.

According to the first aspect of the present invention, when the seating member rolls in the horizontal direction around a swing fulcrum in the horizontal direction of the leg links, the stopper member comes into contact with one of the left and right leg links to prevent the seating member from further tilting in the horizontal direction. Since the tilt in the horizontal direction of the seating member is limited, the stability in the horizontal direction of the seating member is improved.

According to the second aspect of the present invention, the seating member is maintained in the posture orthogonal to the equiangular bisector of the angle in the horizontal direction formed by the left and right leg links by the regulating mechanism. Therefore, in the second aspect, the stability in the horizontal direction of the seating member is also improved. In the second aspect, the stopper member in the first aspect is unnecessary.

In the first aspect of the present invention, when the left and right leg links are wide open in the horizontal direction, the seating member greatly tilts in the horizontal direction until the stopper member comes into contact with the leg links. Therefore, in the first aspect, it is desirable that the walk supporting device includes urging means for urging the stopper member in a direction in which angles in the horizontal direction formed by the left and right leg links and the stopper member are equal. Consequently, the seating member is elastically maintained in the posture orthogonal to the equiangular bisector of the angle in the horizontal direction formed by the left and right leg links. Therefore, the stability in the horizontal direction of the seating member is improved in the state in which the left and right leg links are wide open in the horizontal direction.

When the walk supporting device includes the urging means, it is desirable that the seating member is formed such that a center of gravity position of the seating member including the stopper member is located below the swing fulcrum in the horizontal direction of the leg links. Consequently, when the equiangular bisector of the angle in the horizontal direction formed by the left and right leg links tilts in the horizontal direction with respect to a vertical line passing the swing fulcrum in the horizontal direction of the leg links, the moment around the swing fulcrum is generated by the weight of the seating member and the stopper member shifts to the vertical line side with respect to the equiangular bisector. The equiangular bisector tilts in the horizontal direction with respect to the vertical line when the user turns an idling leg outward in a one-leg supported state. In this case, when the stopper member shifts to the vertical line side with respect to the equiangular bisector, the tilt in the horizontal direction of the seating member remains small and a better feeling of wearing is obtained.

DETAILED DESCRIPTION OF THE PREFERRED EMBODIMENTS

Figure 1:
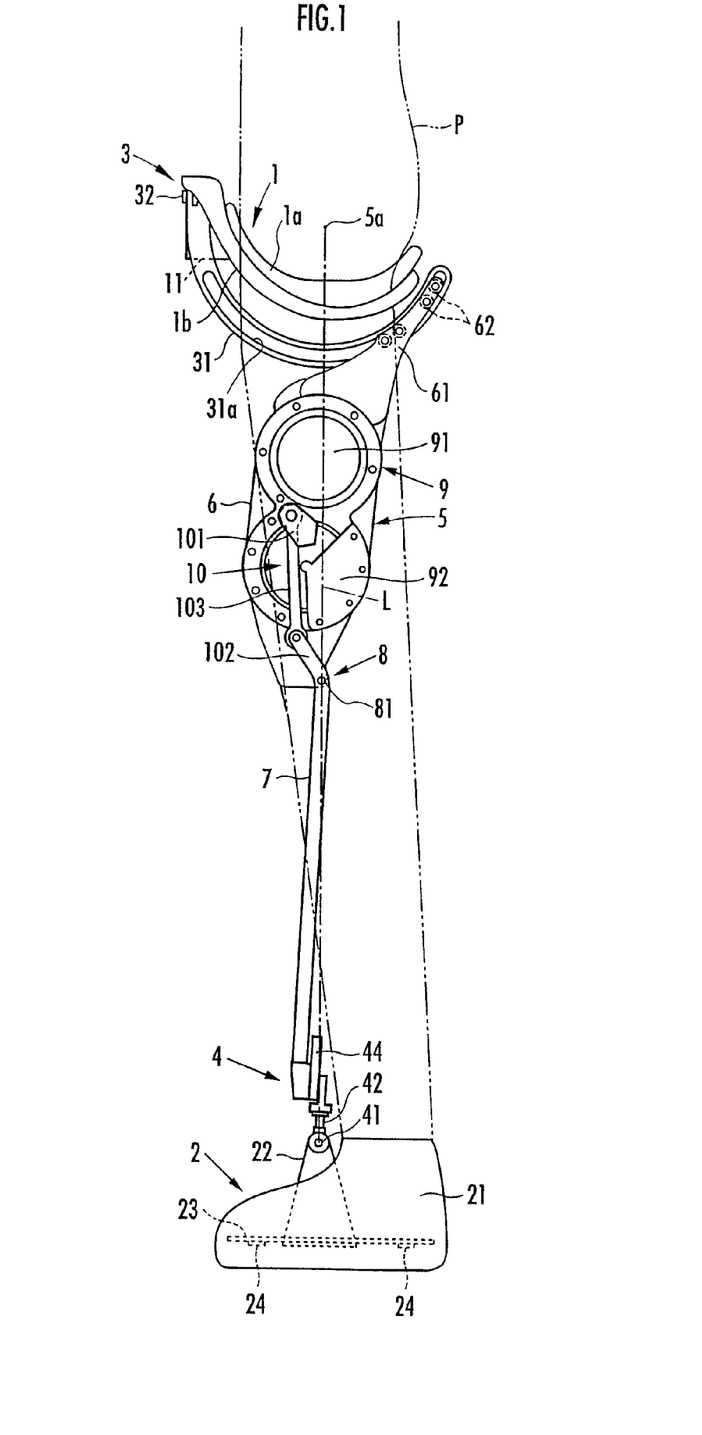
FIG. 1 is a side view of a walk supporting device according to a first embodiment of the present invention.
Figure 2:
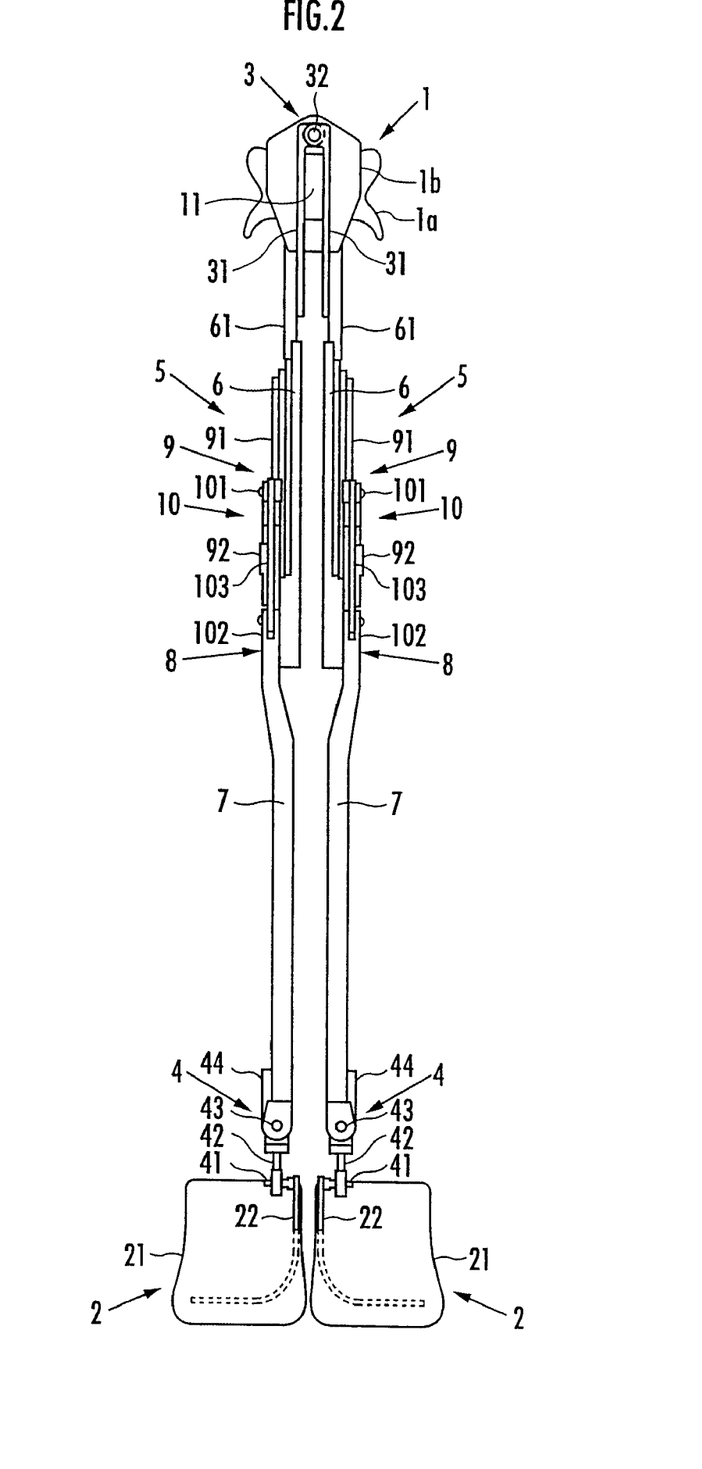
FIG. 2 is a front view of the walk supporting device according to the first embodiment.

A walk supporting device according to an embodiment of the present invention will be hereinafter explained. As shown in FIGS. 1 and 2, the walk supporting device includes a seating member 1 on which a user P is seated in a straddling manner, a pair of left and right foot worn members 2 worn on the left and right feet of the user, and a pair of left and right leg links 5 that are coupled to the seating member 1 via a first joint section 3 at an upper end thereof and coupled to the both foot worn members 2 via second joint sections 4 at a lower end thereof, respectively, and support the seating member 1 from below.

Each of the leg links 5 is constituted by a stretchable link that changes a distance between the first joint section 3 and the second joint section 4. In each of the leg links 5, an upper first link section 6 coupled to the seating member 1 via the first joint section 3 and a lower second joint section 7 coupled to the foot worn member 2 via the second joint section 4 are stretchably coupled by a rotary third joint section 8. Each of the leg links 5 is mounted with a driving source 9 for the third joint section 8. A force in a direction for increasing the distance between the first joint section 3 and the second joint section 4, i.e., a force in a direction for stretching each of the leg links 5 is applied to each of the leg links 5 according to driving of the third joint section 8 by the driving source 9 to cause the leg link 5 to generate a supporting force for supporting at least a part of a body weight of the user P (hereinafter referred to as body weight relief assist force). The body weight relief assist force generated by each of the leg links 5 is transmitted to a trunk of the user P via the seating member 1, whereby a load acting on the leg of the user P is reduced.

The user P can use the walk supporting device according to this embodiment simply by wearing the foot worn members 2 on the feet and being seated on the seating member 1. Thus, the user P hardly feels restraint. Since the leg links 5 are located in the inner side of leg of the user P, the hands do not hit the leg links 5 when the user P swings the arms during walk and the user P can freely swing the arms. Moreover, since the walk supporting device is small, it is possible to use the walk supporting device even in a narrow place and convenience of use is remarkably improved in conjunction with the reduction in the restraint and the ensuring of the freedom of swing of arms.

The seating member 1 includes a seat section 1a of a saddle shape on which the user P is seated and a seat frame 1b on a lower side of the seat 1a. Each of the leg links 5 includes a joint member 31 for the first joint section 3 at an upper end thereof. An arcuate guide track 31a long in a front to rear direction is formed in this joint member 31. A slider 61 is coupled to the upper end of the first link section 6 of each of the leg links 5. The slider 61 is engaged with the guide track 31a via plural rollers 62 pivotally attached to the slider 61 to freely move. In this way, each of the leg links 5 can freely swing in the front to rear direction around a center of curvature of the guide track 31a.

Referring to FIG. 1, the center of curvature of the guide track 31a, i.e., a swing fulcrum 5a in the front to rear direction of each of the leg links 5 is located above the seating member 1. When, for example, the user P tilts the upper part of the body forward and a point of action of the weight of the upper half of the user P shifts to the front of the swing fulcrum 5a in the front to rear direction of each of the leg links 5, the seating member 1 inclines down forward. When the seating member 1 continues to incline, the seating member 1 shifts backward with respect to the user P. However, in this embodiment, the point of action of the body weight is displaced backward on the lower side of the swing fulcrum 5a as the seating member 1 inclines down forward, the distance in the front to rear direction between the fulcrum 5a and the point of action of the body weight decreases, and a rotation moment acting on the seating member 1 also decreases. When the point of action of the body weight is displaced to a position right below the swing fulcrum 5a, the rotation moment acting on the seating member 1 decreases to zero. In this state, the seating member 1 is stabilized. In this way, the seating member 1 automatically settles in the stable state. Thus, it is possible to prevent the seating member 1 from shifting in the front to rear direction in the inner side of the leg of the user P.

The slider 61 of each of the leg links 5 is engaged with a portion of the guide track 31a located behind a line connecting the third joint section 8 of each of the leg links 5 and the swing fulcrum 5a in the front to rear direction of each of the leg links 5. Consequently, it is possible to secure a swing stroke to the front of each of the leg links 5, which follows swing-out to the front of each leg of the user P, without substantially increasing the length of the guide track 31a.

The first joint section 3 includes a support shaft 32 in the front to rear direction fixed to a rising portion at a front end of the seat frame 1b of the seating member 1. The joint members 31 at the upper ends of the left and right leg links 5 are supported by the support shaft 32 in rising portions at front ends thereof to freely swing in the horizontal direction. Therefore, each of the leg links 5 is coupled to the seating member 1 via each of the joint members 31 to freely swing in the horizontal direction and can turn the leg of the user P outward.

Each of the foot worn members 2 includes a shoe 21 and a coupling member 22 projected upward from the inside of the shoe 21. A second link section 7 of each of the leg links 5 is coupled to this coupling member 22 via the second joint section 4. The second joint section 4 has a three-axis structure including a first shaft 41 in the horizontal direction, a second shaft 42 in the vertical direction, and a third shaft 43 in the front to rear direction. A biaxial force sensor 44 is built in the second joint section 4. The body weight relief assist force acts on a line connecting the swing fulcrum 5*a* in the front to rear direction of the leg link 5 and the first shaft 41 of the second joint section 4 (hereinafter referred to as reference line) L viewed from the horizontal direction. An actual body weight relief assist force (accurately, a resultant force of the body weight relief assist force and a force generated by the weight of the seating member 1 and each of the leg links 5) acting on the reference line L is calculated on the basis of detection values of forces in two axial directions detected by the force sensor 44.

As shown in FIG. 1, a pair of front and rear pressure sensors 24 that detect loads acting on a metatarsophalangeal joint (MP joint) and a heel portion of the foot of the user P are attached to a lower surface of an insole 23 provided in the shoe 21.

In walk assist control, first, on the basis of detection values of both the pressure sensors 24 of each of the foot worn members 2, a ratio of a load acting on each of the feet to a total load acting on both the feet of the user P is calculated. Subsequently, a value obtained by multiplying a set value of a body weight relief assist force set in advance by the load ratio of each of the feet is calculated as a control target value of a body weight relief assist force that should be generated in each of the leg links 5. The driving source 9 is controlled such that the actual body weight relief assist force calculated on the basis of the detection value of the force sensor 44 reaches the control target value.

The driving source 9 includes an electric motor 91 and a reduction gear 92 of a planetary gear type. The third joint section 8 is driven by the electric motor 91 via the reduction gear 92 and a power transmitting mechanism 10. The third joint section 8 pivotally attaches the upper end of the second link section 7 to the lower end of the first link section 6 via a joint shaft 81 in the horizontal direction. The power transmitting mechanism 10 includes a first crank arm section 101 provided on an output side of the reduction gear 92, a second crank arm section 102 integrally provided with the second link section 7 extending upward from the joint shaft 81, and a rod 103 that couples both the crank arm sections 101 and 102. Consequently, a rotation output of the reduction gear 92 is transmitted to the second crank arm section 102 via the first crank arm section 101 and the rod 103. The second link section 7 swings with respect to the first link section 6 around the joint shaft 81 and the leg link 5 is bent and stretched.

In this embodiment, in a one-leg supporting state, in order to prevent the seating member 1 from rolling in the horizontal direction around the swing fulcrum in the horizontal direction of the leg link 5 on a supporting leg (a leg, a foot of which is on the floor) side because of the weight of the leg link 5 on an idling leg (a leg, a foot of which is left from the floor) side, the left and right leg links 5 are supported by the common support shaft 32 to freely swing in the horizontal direction. However, in a both-leg supporting state, the seating member 1 is capable of rolling in the horizontal direction around the support shaft 32 and it is likely that the seating member 1 greatly tilts in the horizontal direction.

Thus, in this embodiment, the stopper member 11 coupled to the seating member 1 is inserted between the left and right leg links 5. More specifically, the stopper member 11 located below the support shaft 32 is fixed in the rising portion at the front end of the seat frame 1*b* of the seating member 1. The stopper member 11 is inserted between the joint members 31 provided at the upper ends of the left and right leg links 5.

Consequently, the rolling in the horizontal direction of the seating member 1 around the support shaft 32 is limited by the contact of the stopper member 11 with each of the joint members 31 and stability in the horizontal direction of the seating member 1 is improved. In this embodiment, the stopper member 11 is formed of a board material. However, it is also possible that the stopper member 11 is formed in a box shape and accessories such as a motor driver provided in the walk supporting device are stored in the stopper member 11.

In the walk supporting device according the first embodiment, when the left and right leg links 5 are greatly opened in the horizontal direction, the seating member 1 greatly tilts in the horizontal direction until the stopper member 11 comes into contact with each of the joint members 31. Thus, an embodiment in which it is possible to improve the stability in the horizontal direction of the seating member 1 even in the state in which the left and right leg links 5 are greatly opened in the horizontal direction will be hereinafter explained.

Figure 3:
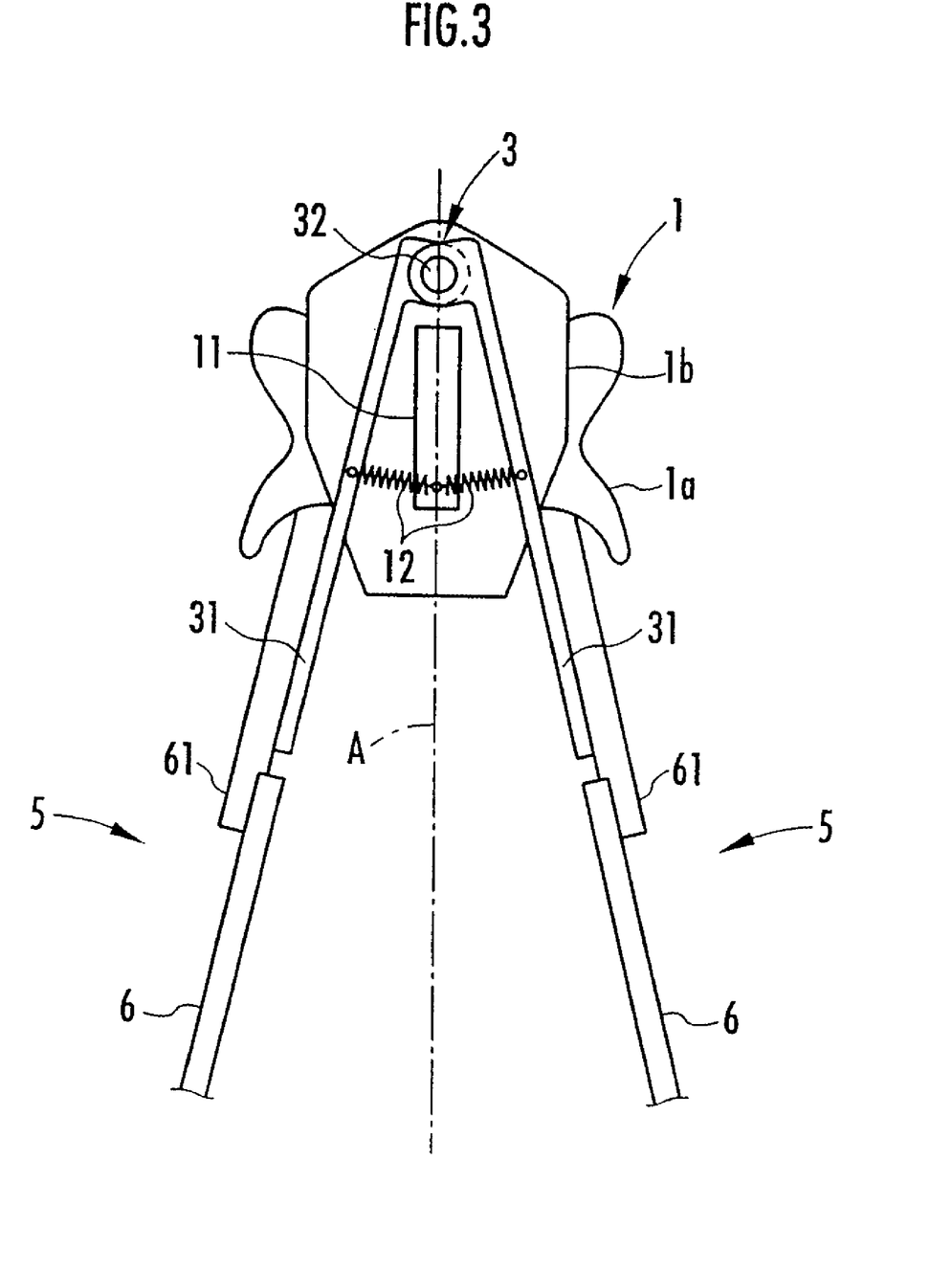
FIG. 3 is an enlarged front view of a main part of a walk supporting device according to a second embodiment of the present invention.

In a second embodiment shown in FIG. 3, urging means for urging the stopper member 11 in a direction in which angles formed by the left and right leg links 5 and the stopper member 11 are equal is provided. More specifically, tension springs 12 as the urging means are tensed between the joint members 31 of the left and right leg links 5 and the stopper member 11.

Consequently, the stopper member 11 is urged, according to a balance of an urging force of one tension spring 12 acting between the joint member 31 of one of the left and right leg links 5 and the stopper member 11 and an urging force of the other tension spring 12 acting between the joint member 31 of the other leg linker 5 and the stopper member 11, in the direction in which the angles in the horizontal direction formed by the left and right leg links 5 and the stopper member 11 are equal. Thus, the seating member 1 is elastically supported in a posture orthogonal to an equiangular bisector A of the angle in the horizontal direction formed by the left and right leg links 5. Therefore, the stability in the horizontal direction of the seating member 1 in the state in which the left and right leg links 5 are greatly opened in the horizontal direction is improved. It is also possible to interpose compression springs between the joint members 31 of the left and right leg links 5 and the stopper member 11 and constitute urging means with these compression springs.

The urging means only has to be constituted such that the stopper member 11 is urged in a direction in which an angle in the horizontal direction formed by the stopper member 11 and one of the left and right leg links 5 and an angle in the horizontal direction formed by the stopper member 11 and the other leg link 5 are equal. It is not requested that both the angles are actually equal. For example, the seating member 1 is formed such that a center of gravity position of the seating member 1 including the stopper member 11 is located below the support shaft 32 serving as the swing fulcrum in the horizontal direction of the leg links 5. In this case, when the equiangular bisector A of the angle in the horizontal direction formed by the left and right leg links 5 tilts in the horizontal direction with respect to a vertical line passing the support shaft 32, a moment around the support shaft 32 due to the weight of the seating member 1 is generated and the stopper member 11 shifts to the vertical line with respect to the equiangular bisector A. Therefore, both the angles are unequal, which advantageously works in improving the feeling of wearing. In other words, the equiangular bisector A tilts in the horizontal direction with respect to the vertical line when the idling leg is turned outward in the one-leg supporting state. In this case, when the stopper member 11 shifts to the vertical line side with respect to the equiangular bisector A, the tilt in the horizontal direction of the seating member 1 remains small and a better feeling of wearing is obtained.

Figure 4:
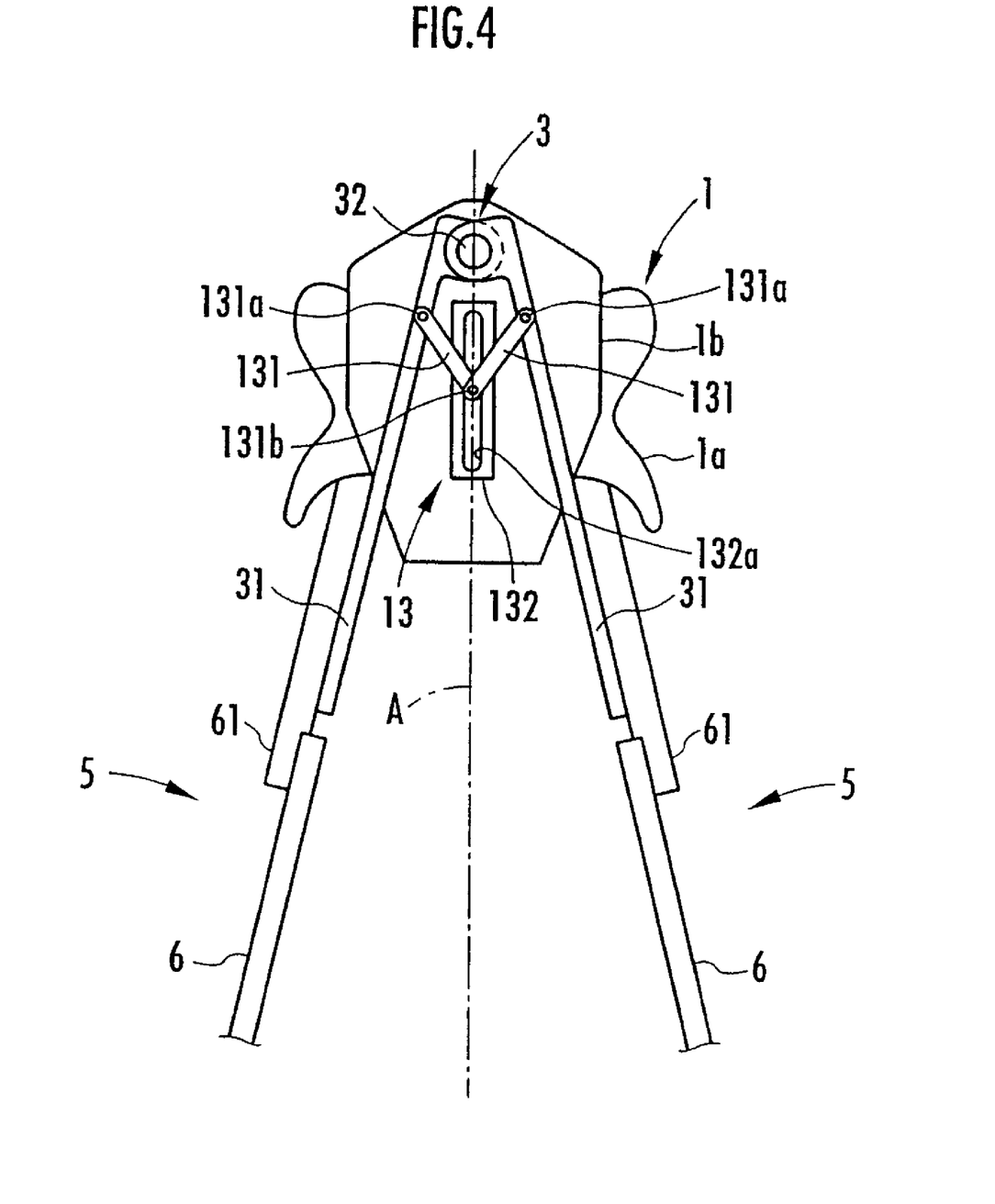
FIG. 4 is an enlarged front view of a main part of a walk supporting device according to a third embodiment of the present invention.

A third embodiment shown in FIG. 4 will be explained. In the third embodiment, a regulating mechanism 13 that regulates the seating member 1 in the posture orthogonal to the equiangular bisector A of the angle in the horizontal direction formed by the left and right leg links 5 is provided. This regulating mechanism 13 includes a pair of short links 131 having an equal length, one ends of which are pivotally attached to the joint members 31 of the left and right leg links 5 by a shaft 131a, respectively, and a guide member 132 having a guide groove 132a long in the vertical direction that is located and fixed right below the support shaft 32 of the seat frame 1b of the seating member 1. A shaft 131b that couples the other ends of both the short links 131 is engaged with the guide groove 132a to freely slide.

The shaft 131b moves in the vertical direction when the angle in the horizontal direction formed by the left and right leg links 5 changes. Since both the short links 131 have the same length, a moving locus of the shaft 131b coincides with the equiangular bisector A of the angle in the horizontal direction formed by the left and right leg links 5. Therefore, the guide member 132 engaged with the shaft 131b is also positioned to coincide with this equiangular bisector A. As a result, the seating member 1 is regulated in the posture orthogonal to the equiangular bisector A. Therefore, the seating member 1 does not roll in the horizontal direction and the stability in the horizontal direction of the seating member 1 is improved.

In the first to third embodiments, the left and right leg links 5 are supported by the common support shaft 32 to freely swing in the horizontal direction. It is also conceivable to support one of the left and right leg links 5 and the other leg link 5 to freely swing in the horizontal direction with separate support shafts spaced apart in the horizontal direction. However, in this walk supporting device, in the two-leg supporting state, the left and right leg links 5 can move in the horizontal direction in a parallel link manner and the seating member 1 can be displaced in the horizontal direction. In this case, as in the first embodiment, if the stopper member 11 coupled to the seating member 1 is inserted between the left and right leg links 5, it is possible to prevent, with the stopper member 11, each of the leg links 5 from swinging by a predetermined angle or more inward in the horizontal direction with respect to the seating member 1. Therefore, the displacement in the horizontal direction of the seating member 1 in the two-leg supporting state is controlled and the stability in the horizontal direction of the seating member 1 is improved.

It is also possible to prevent the displacement in the horizontal direction of the seating member 1 by elastically maintaining or regulating the seating member 1 in the posture orthogonal to the equiangular bisector A of the angle in the horizontal direction formed by the left and right leg links 5 as in the second and third embodiments. When the left and right leg links 5 are supported by the separate support shafts to freely swing in the horizontal direction, it is also possible to adopt a mechanism same as that in the third embodiment as the regulating mechanism 13 that regulates the seating member 11 in the posture orthogonal to the equiangular bisector A of the angle in the horizontal direction formed by the left and right leg links 5. It is also possible to adopt more simple mechanisms shown in FIGS. 5 and 6, which will be explained below.

Figure 5:
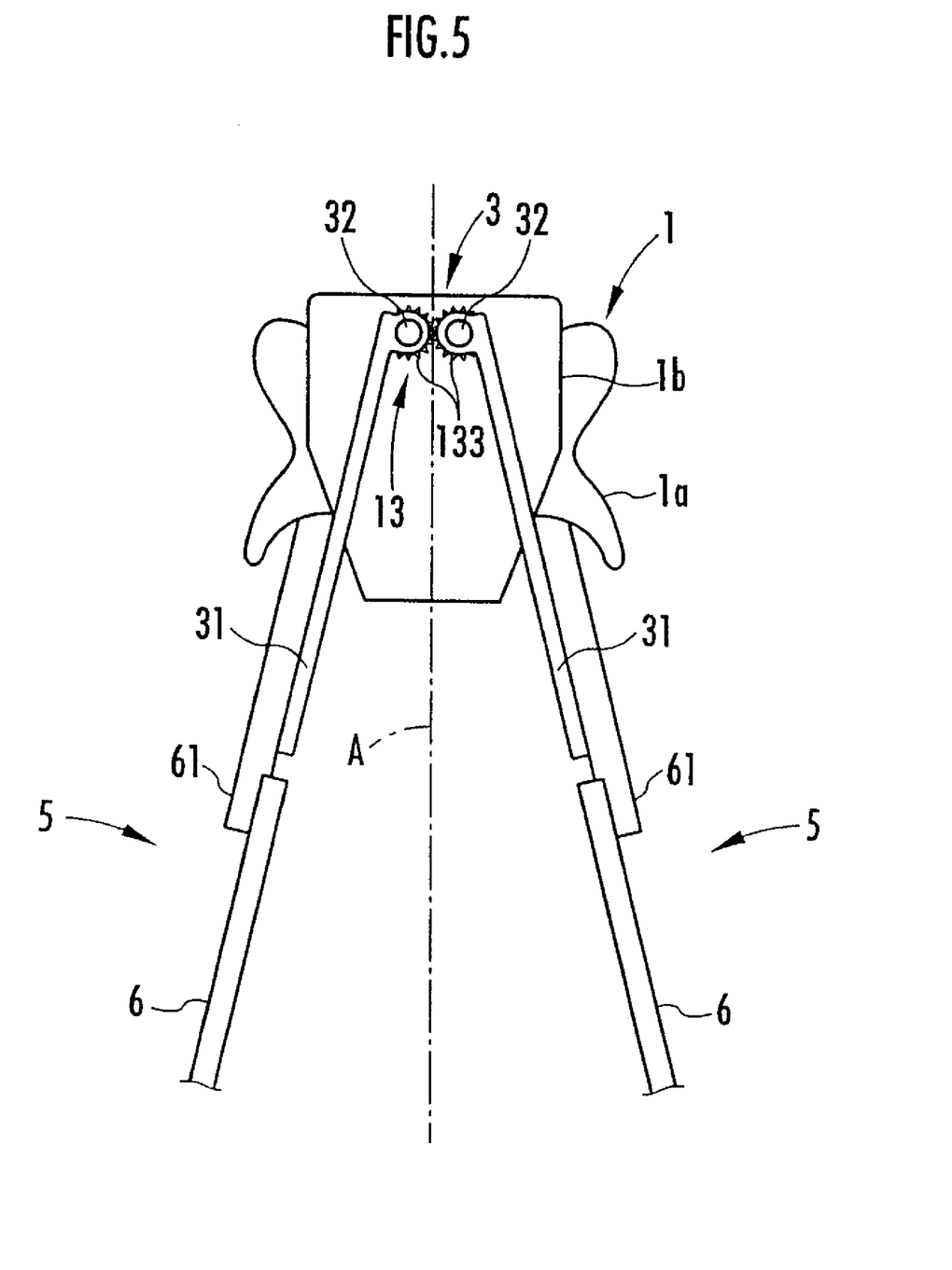
FIG. 5 is an enlarged front view of a main part of a walk supporting device according to a fourth embodiment of the present invention.

In a fourth embodiment shown in FIG. 5, gears 133 concentric with the separate support shafts 32 that support the joint members 31, respectively, are formed in the joint members 31 of the left and right leg links 5. The regulating mechanism 13 is constituted by meshing both the gears 133 with each other. In a fifth embodiment shown in FIG. 6, pulleys 134 concentric with the separate support shafts 32 that support the joint members 31, respectively, are fixed to the joint members 31 of the left and right leg links 5. The regulating mechanism 13 is constituted by laying a belt 135 over the pulleys 134 in a crossing manner.

Figure 6:
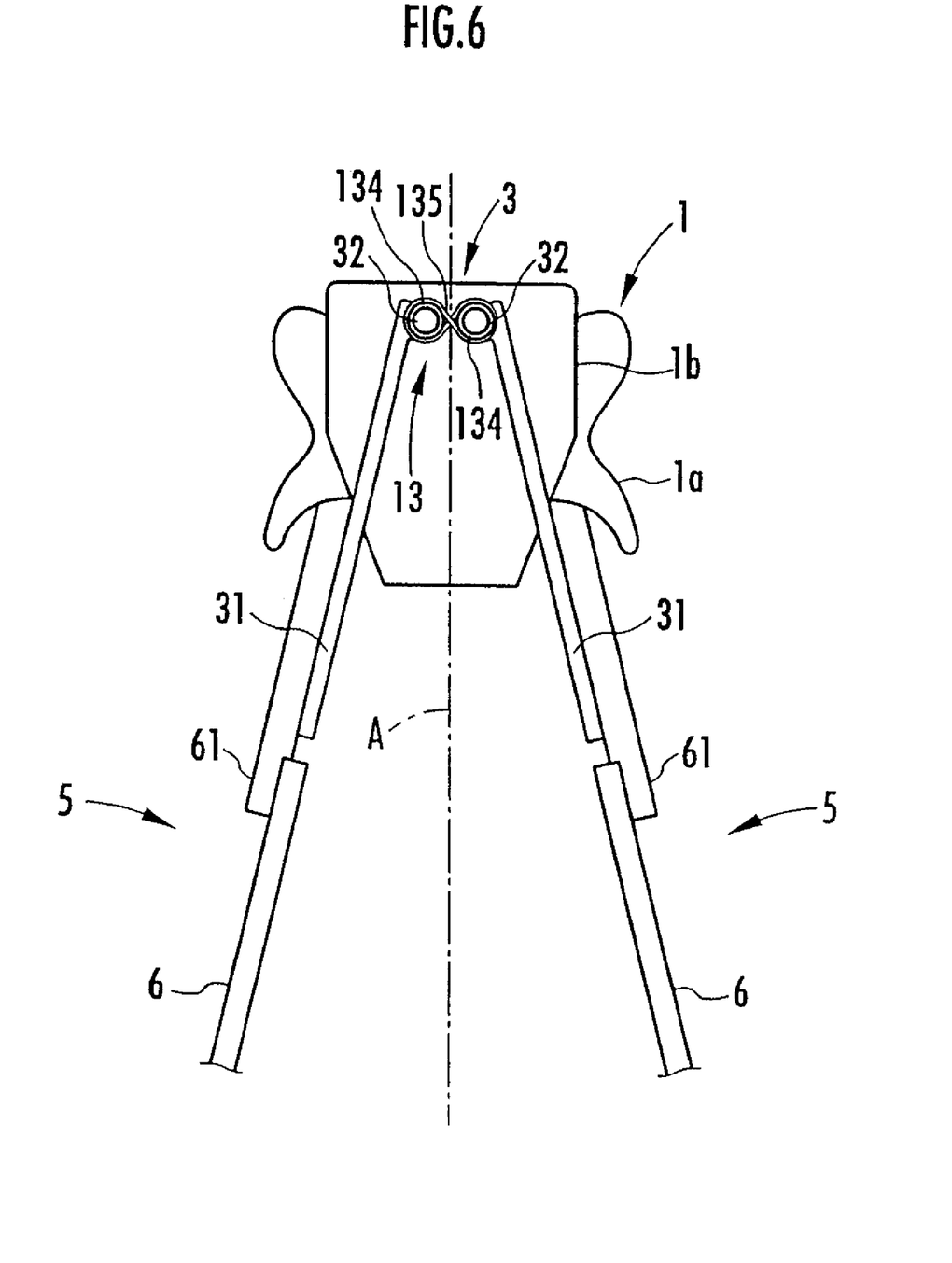
FIG. 6 is an enlarged front view of a main part of a walk supporting device according to a fifth embodiment of the present invention.

In both the fourth and fifth embodiments, the left and right leg links 5 swing at an equal angle in opposite directions. Therefore, angles formed by the left and right leg links 5 and a perpendicular line passing a midpoint of a connection linking the support shafts 32 of both the leg links 5 are equal. In other words, this perpendicular line coincides with the equiangular bisector A of the angle in the horizontal direction formed by the left and right leg links 5. Therefore, the seating member 1 is regulated in the posture orthogonal to this equiangular bisector A. Consequently, it is possible to prevent the displacement in the horizontal direction of the seating member 1 and the stability in the horizontal direction of the seating member 1 is improved.

The embodiments of the present invention have been explained with reference to the drawings. However, the present invention is not limited to the embodiments. For example, in the embodiments, the foot worn member 2 is coupled to the lower end of each of the leg links 5. However, it is also possible to fix the lower end of each of the leg links 5 to the lower thigh of each of the user's legs and generate a body weight relief assist force using a portion of the leg lower than this fixing portion as a reaction receiver. In the embodiments, each of the leg links 5 is constituted by the stretchable link having the rotary third joint section 8 in the middle. However, each of the leg links 5 may be constituted by stretchable link having the third joint section 8 as a direct-acting joint section. Moreover, it is also possible to provide urging means for urging the third joint section 8 in an extending direction (a direction in which a distance between the first joint section 3 and the second joint section 4 is increased) and eliminating the driving source 9 for the third joint section 8.

What is claimed is:

1. A walk supporting device comprising:
   a seating member adapted to receive a user seated in a straddling manner;
   a pair of left and right leg links that support the seating member from below, each of the leg links being coupled to the seating member to freely swing in a horizontal side-to-side direction, wherein a swing fulcrum of the leg links is located above the seating member and a stopper member coupled to the seating member is inserted between the left and right leg links and is adapted to limit swinging of the seating member in the horizontal side-to-side direction; and
   urging means for urging the stopper member in a horizontal side-to-side direction in response to a horizontal side-to-side swinging of at least one of the left and right leg links such that angles in the horizontal side-to-side direction formed by the left and right leg links and the stopper member are equal, wherein the urging means tenses the stopper member between the left and right leg links.

2. The walk supporting device according to claim 1, wherein the seating member is formed such that a center of gravity position of the seating member including the stopper member is located below a swing fulcrum in the horizontal side-to-side direction of the leg links.

3. The walk supporting device according to claim 2, wherein the stopper member is disposed so as to make contact with at least one of the left and right leg links when said at least one of the left and right leg links swings horizontally inwardly toward the other leg link and the stopper member.

4. The walk supporting device according to claim 1, wherein the stopper member is disposed so as to make contact with at least one of the left and right leg links when said at least one of the left and right leg links swings horizontally inwardly toward the other leg link and the stopper member.

5. A walk supporting device comprising:
a seating member adapted to receive a user seated in a straddling manner; and
a pair of left and right leg links that support the seating member from below,
each of the leg links being coupled to the seating member to freely swing in a horizontal side-to-side direction, wherein
a swing fulcrum of the leg links is located above the seating member, and
a stopper member coupled to the seating member is inserted between the left and right leg links and is adapted to limit swinging of the seating member in the horizontal side-to-side direction.

6. The walk supporting device according to claim 5, wherein the stopper member is disposed so as to make contact with at least one of the left and right leg links when said at least one of the left and right leg links swings horizontally inwardly toward the other leg link and the stopper member.

7. The walk supporting device according to claim 5, wherein the leg links are coupled to the seating member so as to freely swing in both the horizontal side-to-side direction and a front-to-rear direction.

8. A walk supporting device comprising:
a seating member that is adapted to receive a user seated in a straddling manner; and
a pair of left and right leg links that support the seating member from below,
each of the leg links being coupled to the seating member to freely swing in a horizontal side-to-side direction, wherein
a swing fulcrum of the leg links is located above the seating member, and
the walk supporting device includes a regulating mechanism that, in response to a horizontal swinging of at least one of the left and right leg links, regulates the seating member in a posture orthogonal to an equiangular bisector of an angle in the horizontal side-to-side direction formed by the left and right leg links.

9. The walk supporting device according to claim 8, wherein the leg links are coupled to the seating member so as to freely swing in both the horizontal side-to-side direction and a front-to-rear direction.

* * * * *